United States Patent
Boese et al.

(10) Patent No.: US 7,593,558 B2
(45) Date of Patent: Sep. 22, 2009

(54) METHOD FOR MOVEMENT-COMPENSATION IN IMAGING

(75) Inventors: Jan Boese, Eckental (DE); Martin Kleen, Furth (DE); Marcus Pfister, Bubenreuth (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 710 days.

(21) Appl. No.: 11/402,320

(22) Filed: Apr. 11, 2006

(65) Prior Publication Data

US 2006/0235295 A1 Oct. 19, 2006

(30) Foreign Application Priority Data

Apr. 15, 2005 (DE) .................... 10 2005 017 492

(51) Int. Cl.
*G06K 9/00* (2006.01)
*A61B 5/05* (2006.01)

(52) U.S. Cl. .................. 382/128; 382/275; 600/407

(58) Field of Classification Search ................ 382/100, 382/128, 129, 130, 131, 132, 133, 134, 154, 382/168, 181, 201, 203, 220, 232, 254, 274, 382/275, 276, 305, 312; 324/309; 600/428, 600/407; 378/20, 21, 23
See application file for complete search history.

(56) References Cited

U.S. PATENT DOCUMENTS

| | | | | |
|---|---|---|---|---|
| 6,894,494 B2 * | 5/2005 | Stergiopoulos et al. | ..... | 324/309 |
| 6,950,689 B1 * | 9/2005 | Willis et al. | ................. | 600/407 |
| 7,359,535 B2 * | 4/2008 | Salla et al. | ................... | 382/128 |
| 7,454,043 B2 * | 11/2008 | Eck et al. | .................... | 382/128 |
| 7,467,007 B2 * | 12/2008 | Lothert | ....................... | 600/428 |
| 2005/0226527 A1 * | 10/2005 | Weese et al. | ................ | 382/275 |

FOREIGN PATENT DOCUMENTS

| DE | 102 31 061 A1 | 1/2004 |
|---|---|---|
| DE | 10231061 A1 * | 1/2004 |

* cited by examiner

*Primary Examiner*—Seyed Azarian

(57) ABSTRACT

In a method for mathematical compensation of a periodic movement of an organ in a first image-generation method used to image said organ, two time series of three-dimensional image data are acquired using gating, one by the first image-generation method and one by the second image-generation method, the image data that have been acquired by the second image-generation method being used to calculate motion fields which are applied for the compensation of the data from the time series which was acquired by the first image-generation method. The compensation encompasses the mathematical inclusion of motion fields and the mapping of the image data to a reference time. All the image data mapped back to the reference time are added together.

8 Claims, 1 Drawing Sheet

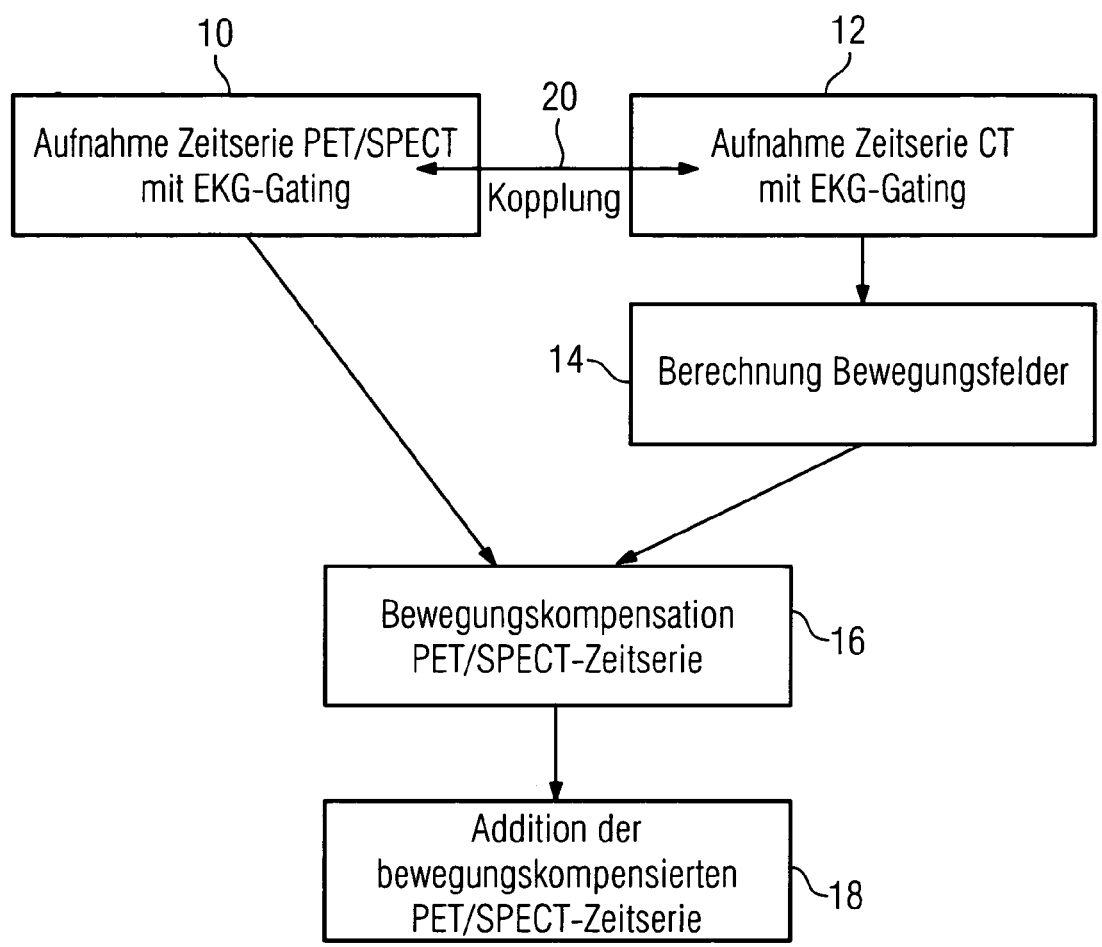

METHOD FOR MOVEMENT-COMPENSATION IN IMAGING

CROSS REFERENCE TO RELATED APPLICATIONS

This application claims priority to the German Application No. 10 2005 017 492.2, filed Apr. 15, 2005 which is incorporated by reference herein in its entirety.

FIELD OF INVENTION

The invention relates to a method for mathematical compensation of a periodic movement of an organ in a first image generation method used for imaging said organ.

It also relates to an image recording system for a first image generation method.

BACKGROUND OF INVENTION

If images are taken of the heart by means of nuclear medical investigation methods such as, for example, PET (Positron Emission Tomography) and SPECT (Single Positron Emission Computer Tomography), this involves long acquisition times typically lasting a few minutes (as in PET) and up to more than 20 minutes (in SPECT). The resulting data set therefore represents a time-related averaging over all the cardiac phases and the cardiac motion therefore appears blurred.

Furthermore, DE 102 31 061 A1 discloses a method for imaging, onto a reference time, three-dimensional image data recorded by means of a first imaging method (PET) and containing motion artifacts, and for compensating for the motion artifacts. To achieve this, a second image generation method (CT) is used, with which a ti me series of image data is recorded, from which motion fields are determined that are used to compensate for the motion artifacts from the first image generation method. The first image generation method claimed in DE 102 31 061 A1 produces only a fuzzy and blurred image, however. This blurring can restrict the usability of the data set for diagnosis.

In order to avoid this effect, an ECG gating can be applied. In an ECG gating, an ECG is taken at the same time as the image data are recorded. ECG gating is based on the fact that the cardiac cycle is repeated. The image data that are recorded during equal intervals of the cardiac cycle are therefore coordinated. Thus a time series of three-dimensional image data is obtained, wherein said image data have always been recorded within a certain interval in the cardiac cycle. The series is achieved by juxtaposing the sequence of images for the respective intervals in the cardiac cycle.

What is then obtained is a plurality of images, with each respective image corresponding to a specific phase of the cardiac cycle. The cardiac motion should always remain the same and therefore no substantial motion blurring should occur in each of the respective individual images.

SUMMARY OF INVENTION

The disadvantage of the method that involves ECG gating is that the number of events measured per individual image is reduced as a result of the division into time intervals. This has a detrimental effect on the signal-to-noise ratio of the images and the diagnostic value of the images is again restricted.

Motion compensation when using individual images recorded by ECG gating is known from the prior art. In this method, the cardiac motion is first determined on the basis of the images. This motion is used to determine motion fields and the different individual images are mapped on a reference image. The motion-corrected individual images are added together and an image is obtained without any motion-related blurring and with a good signal-to-noise ratio. A problem inherent in the above method is that the motion fields can only be determined imperfectly. In fact, nuclear medical images only allow the cardiac motion to be approximated imperfectly. Reasons for this are the low loc al resolution, the low signal-to-noise ratio in nuclear medical images and the absence of characteristic anatomical structures in the images.

An object of the invention is to enable image generation methods that have a long acquisition duration, which is, in particular, longer than the periodic motion of an organ that is to be imaged, and using them more effectively for the diagnosis of these periodically moving organs, and of suggesting an improved method that can be used for mathematical compensation of a periodic movement of an organ in a first image-generation method used to image said organ.

The above object is achieved by the claims.

The method is based on the principle that a second image-generation method is likewise used which serves the purpose of capturing the periodic motion of the organ precisely. This results in the determination of what are known as motion fields. Motion fields are three-dimensional data sets, which assign a three-dimensional vector to each voxel, that is, to each volume element in a three-dimensional image. The aforementioned vector shows the displacement of this volume element, that is, of this voxel, relative to the reference data set. Methods for calculating three-dimensional motion fields, with the aid of the optical flow, for example, are known to a person skilled in the art.

The invention utilizes the fact that the second image-generation method that is used can be selected in such a way that it has considerably shorter acquisition times, has a better signal-to-noise ratio or can image anatomical structures in a better way, such that the motion fields can be better detected from the image data acquired using the image-generation method. The invention takes as its point of departure the fact that, once acquired, the motion fields which reproduce the local variability of individual volume elements are also applicable in an appropriate manner to image data which have been acquired by means of a first image generation method, namely nuclear medical image generation methods such as PET and SPECT. If a motion field correctly reproduces the fact that during the periodic signal, of the cardiac cycle, for example, a specific volume element of the organ being investigated, such as of the heart, for example, moves in a certain direction, then this will also apply to image data recorded in a different way. The motion fields once acquired are then used to correct the image data acquired using the other image-generation method. By means of the motion fields, the three-dimensional image data can be mapped back to a reference time.

In a preferred embodiment the time series determined by means of the two image generation methods are each determined for the same times in the periodic motion. The time series can therefore be mapped one directly on top of another, and the motion fields can be used directly, without any mathematical conversion being required. The image data acquired can then be mapped directly onto three-dimensional image data for a reference time in the periodic motion. Once the time series have been determined at various times in the periodic motion, interpolation methods can be used.

The second image-generation method can encompass in particular a computer tomography method, a rotational X-ray angiography method, a magnetic resonance method or an ultrasound method.

The invention is applicable to the imaging of any organ that moves periodically, in particular, in addition to the heart, to the lung and the respiratory apparatus, respiratory gating then being used instead of ECG gating.

Gating is generally understood as being the allocation of image data to times in a specific interval.

In order to be able to apply motion fields determined using the second image-generation method to the data measured using the first image-generation method, the relationship between the two systems of coordinates must be known. For this, image registration methods known to a person skilled in the art are used.

In a different preferred embodiment, the systems for generating images for the first and the second image-generation method are mechanically connected, so that the three-dimensional data sets can be directly correlated and do not have to be mapped one on top of another on the basis of a registration method.

In the final step of the invention all the image data for the reference time acquired using the first image-generation method are used to produce a single data set for the reference time. In an advantageous manner, all the image data are simply added together.

A further feature of the invention is that the image-recording system for a first image-generation method is mechanically connected to an image-recording system for a second image-generation method. A device is provided for carrying out gating with respect to the periodic signal from an organ that is to be imaged when images are being generated using both image-generation methods. Furthermore, an image-processing device should be available, the device being designed to also calculate the image data motion fields acquired using the second image-generation method and to apply these motion fields mathematically to image data acquired using the first image-generation method. The system can be in particular a combination of a PET and CT system or a SPECT-CT system.

BRIEF DESCRIPTION OF THE DRAWING

A preferred embodiment of the invention will now be described with reference to the drawing. The drawing shows:

FIG. 1 a flow diagram showing the stages in the method according to the invention.

DETAILED DESCRIPTION OF INVENTION

In the preferred embodiment of the invention, a person's heart is being investigated. A combined PET-CT-System or SPECT-CT-system is used, wherein both the parts of the system are mechanically connected to each other, such that the images that are generated with the PET part of the system can be directly correlated with the CT images.

Furthermore, the option of carrying out ECG gating is available, that is, ECG probes can be attached to the patient, and an image evaluation analyses the ECG signal that has been recorded. The ECG signal is divided into a plurality of intervals, each interval corresponding to a specific image from a time series. The system now records image data and, at the same time, the ECG curve. On the basis of the interval in which the heart is located during the recording of the image data, the image data are assigned in the respective interval and in the respective partial image from the time series of image s. Finally a time series of three-dimensional data which fit together to form an image is obtained.

As can be seen in FIG. 1, a corresponding time series is recorded in step 10 using the first image-generation method, in this case the nuclear medical method, that is, PET or SPECT with ECG gating. Subsequently or beforehand and possibly even at the same time, but in any case independently thereof, but likewise using ECG gating, there ensues, in step 12, the imaging of a time series of CT-images. Since the CT images have a good signal-to-noise ratio, have a higher time resolution and show the anatomy of the heart clearly, the cardiac motion can be deduced more clearly on the CT images. In order to map this motion mathematically, what are known as the motion fields are determined. Motion fields are three-dimensional vectors which are assigned to the individual volume elements (voxels) of the three-dimensional image data. They reproduce the relative motion of this volume element with respect to a reference volume element in a reference image. For example, the reference image is the first image recorded in the ECG gating, and this image is then the reference image for the motion fields. The time series recorded in step 10 with PET/SPECT images is now combined with the motion fields calculated in step 14. In step 16, there ensues what is known as the motion compensation of the PET/SPECT-time series. The premise adopted here is that the cardiac motion determined on the basis of the motion fields was likewise present when the PET/SPECT time series was recorded. The motion can then be calculated in the images from the PET/SPECT-time series. This is based on the following consideration: If, for a volume element, the data value from the CT image number two is a function of CT image number 1, $CT_1 = f(CT_2)$, hence the same function also shows the volume elements from the PET/SPECT image, $PET_1 = f(PET_2)$ with an identical f. The motion field now shows the effect of the function f. In step 16, each image from the time series is now calculated down to the reference time, that is, the respective motion field is applied to the image in the opposite direction, optionally using interpolation, if the ECG gating in step 10 was not identical to the ECG gating in step 12 and the time series do not correspond time-wise. A plurality of image data calculated down to the reference time are then available showing in each case the heart in the location that it is in at the reference time, but which were determined on the basis of values recorded at later times in the cardiac cycle.

In step 18, the motion-compensated images from the PET/SPECT time series are now added together, in order to thus optimize the signal-to-noise ratio of the individual image data. An image is obtained of the heart at the reference time having a high signal-to-noise ratio, which is now more suitable for diagnosis.

To recap in brief, the invention relies on the fact that by means of CT, a calculation of the cardiac motion is made possible, on the basis of which a correction is then made to the PET or SPECT images, the basis thereof being the use of an ECG gating for both time series, said gating being preferably connected together, see the arrow 20.

The invention claimed is:

1. An method of compensating for a periodic movement of an organ recorded, the method comprising:

acquiring a first sequence of three-dimensional image data of the organ by a first imaging mechanism using a gating based on a periodic signal originating from the organ;

acquiring a second sequence of three-dimensional image data of the organ by a second imaging mechanism using the gating;

calculating a plurality of motion fields relative to a reference point in time related to the periodic movement of the organ based on the second sequence;

mapping the first sequence to a reference sequence using the calculated motion fields, the reference sequence having a reference sequence of three-dimensional image data relative to the reference point in time; and generating a single image data set based on the reference sequence, the single image data set representing the organ at the reference point in time;

wherein the single image data set is generated by adding up corresponding voxels of the three-dimensional image data of the reference sequence.

2. The method according to claim 1, wherein the first and second sequences are acquired with respect to identical points in time relative to the periodic movement.

3. The method according to claim 1, wherein the first imaging mechanism is a positron emission tomography (PET) or a single photon emission computed tomography (SPECT).

4. The method according to claim 1, wherein the second imaging mechanism is a computer tomography (CT), a rotational X-ray angiography, a magnetic resonance (MR) method or an ultrasound method.

5. The method according to claim 1, further comprising registering a first coordinate system related to the first imaging mechanism with a second coordinate system related to the second imaging mechanism.

6. The method according to claim 1, wherein the first and second imaging mechanisms are implemented in a first respectively second imaging system, the first and second imaging system mechanically connected to each other.

7. The method according to claim 1, wherein the organ is a human heart, and the gating is an electrocardiogram (ECG) gating.

8. The method according to claim 1, wherein the organ is a human respiratory system, and the gating is a respiratory gating.

* * * * *